(12) United States Patent
Bartlett

(10) Patent No.: US 9,747,770 B1
(45) Date of Patent: Aug. 29, 2017

(54) CHILD TRACKING DEVICE

(71) Applicant: Albertha Bartlett, Fort Lauderdale, FL (US)

(72) Inventor: Albertha Bartlett, Fort Lauderdale, FL (US)

( * ) Notice: Subject to any disclaimer, the term of this patent is extended or adjusted under 35 U.S.C. 154(b) by 0 days.

(21) Appl. No.: 15/177,702

(22) Filed: Jun. 9, 2016

(51) Int. Cl.
| | | |
|---|---|---|
| *G08B 21/02* | (2006.01) | |
| *G08B 25/01* | (2006.01) | |
| *A61B 5/00* | (2006.01) | |
| *G06F 19/00* | (2011.01) | |

(52) U.S. Cl.
CPC ..... *G08B 21/0269* (2013.01); *G08B 21/0266* (2013.01); *G08B 21/0288* (2013.01); *G08B 21/0291* (2013.01); *G08B 21/0294* (2013.01); *G08B 25/016* (2013.01); *A61B 5/742* (2013.01); *G06F 19/3418* (2013.01)

(58) Field of Classification Search
CPC ............ G08B 21/0269; G08B 21/0291; G08B 21/0266; G08B 21/0288; G08B 21/0294; G08B 25/016; A61B 5/742; G06F 19/3418
See application file for complete search history.

(56) References Cited

U.S. PATENT DOCUMENTS

| | | | |
|---|---|---|---|
| 5,617,074 A | 4/1997 | White | |
| 5,900,817 A | 5/1999 | Olmassakian | |
| 5,995,007 A * | 11/1999 | Borja | G08B 21/0288 340/539.1 |
| 6,271,757 B1 * | 8/2001 | Touchton | A01K 15/02 119/721 |
| 6,888,464 B1 * | 5/2005 | Maloney | G08B 21/0288 340/539.1 |
| 7,012,522 B1 | 3/2006 | Le Van | |
| 7,511,627 B2 * | 3/2009 | Holoyda | G08B 21/0202 340/573.4 |
| 7,696,887 B1 * | 4/2010 | Echavarria | G08B 21/0227 340/573.1 |
| 8,321,124 B2 | 11/2012 | Curatolo et al. | |
| 2004/0046658 A1 * | 3/2004 | Turner | G08B 21/0227 340/539.11 |
| 2005/0280546 A1 * | 12/2005 | Ganley | G08B 13/1427 340/573.4 |
| 2010/0267361 A1 * | 10/2010 | Sullivan | G01S 19/17 455/404.2 |
| 2015/0109126 A1 * | 4/2015 | Crawford | G08B 21/0269 340/539.13 |
| 2015/0356861 A1 * | 12/2015 | Daoura | G08B 21/0277 340/539.13 |

* cited by examiner

*Primary Examiner* — Mohamed Barakat
(74) *Attorney, Agent, or Firm* — Stevenson IP, LLC

(57) ABSTRACT

A child tracking device including a wrist watch lockable onto a child's wrist in operational communication with a remote monitoring receiver unit with a liquid crystal display (hereinafter "LCD") screen and a remote mobile device, such as a cellular phone, via a software application to continuously track a child's location and to provide an alert in the event the child strays a pre-set distance from either the remote monitoring receiver unit or the remote mobile device or leaves a designated geographical zone.

6 Claims, 4 Drawing Sheets

CHILD TRACKING DEVICE

BACKGROUND OF THE INVENTION

Various types of proximity monitors for locating a child are known in the prior art. However, what is needed and what the present device provides is a child tracking device including a wrist watch lockable onto a child's wrist in operational communication with a remote monitoring receiver unit with a liquid crystal display (hereinafter "LCD") screen and a remote mobile device, such as a cellular phone, via a software application to continuously track a child's location and to provide an alert in the event the child strays a pre-set distance from either the remote monitoring receiver unit or the remote mobile device.

FIELD OF THE INVENTION

The present invention relates to proximity monitors, and more particularly, to a child tracking device.

SUMMARY OF THE INVENTION

The general purpose of the present child tracking device, described subsequently in greater detail, is to provide a child tracking device which has many novel features that result in a child tracking device which is not anticipated, rendered obvious, suggested, or even implied by prior art, either alone or in combination thereof.

To accomplish this, the present child tracking device is devised to continuously monitor a distance of a child from a supervising adult by including a child-worn wrist watch having a central liquid crystal display, at least one control button as well as a global positioning system receiver, a transmitter, and a first central processing unit within the wrist watch. The first central processing unit is in operational communication with the central liquid crystal display, the at least one control button, the global positioning receiver, and the transmitter. First and second portions of the wrist band are interconnected by a safety clasp lock to prevent the wrist watch from being easily removed by the child wearing the wrist watch or by a kidnapper.

A remote monitoring receiver unit for use by the supervising adult to monitor the child's location includes a receiver in wireless communication with the wrist watch, an LCD receiver display, an LCD monitor, at least one control switch, and a second central processing unit in operational communication with the receiver, the LCD receiver display, the LCD monitor, and the at least one control switch. A remote mobile device, such as a cellular phone, for use by the supervising adult to monitor the child's location includes a receiver unit in wireless operational communication with the wrist watch, a remote LCD display, and a third central processing unit with at least one software application installed thereon and in operational communication with the receiver unit and the remote LCD display. The wrist watch central processing unit calculates the distance a signal from the transmitter traveled to be received by each of the receiver disposed within the remote monitoring unit and the receiver unit disposed within the remote mobile device.

Upon calculation of a distance traveled by the signal greater than a predetermined safe distance from each of the receiver and the receiver unit, an alert notification is displayed on each of the LCD receiver display, the LCD monitor, and the remote LCD display. The at least one software application includes a global positioning system navigation map displayed on the remote mobile device, wherein the global positioning navigation map is configured to display the global position of a wearer of the wrist watch, and wherein the software application is configured to maintain a continuous record of the global position of the wearer of the wrist watch. In addition, the at least one software application is configured to permit designation of a geographical zone on the global positioning system navigation map. Upon the designation of a geographical zone, if the wearer of the wrist watch is located outside of the geographical zone, an alert message is displayed on each of the LCD receiver display, the LCD monitor, and the remote LCD display.

In the instance of an elderly individual wearing the wrist watch 20, the calculation of no distance traveled by the signal, an alert is displaed on each of the LCD receiver display, the LCD monitor, and the remote LCD display.

Thus has been broadly outlined the more important features of the present child tracking device so that the detailed description thereof that follows may be better understood and in order that the present contribution to the art may be better appreciated.

BRIEF DESCRIPTION OF THE DRAWINGS

Figures

DETAILED DESCRIPTION OF THE DRAWINGS

Figure 1:
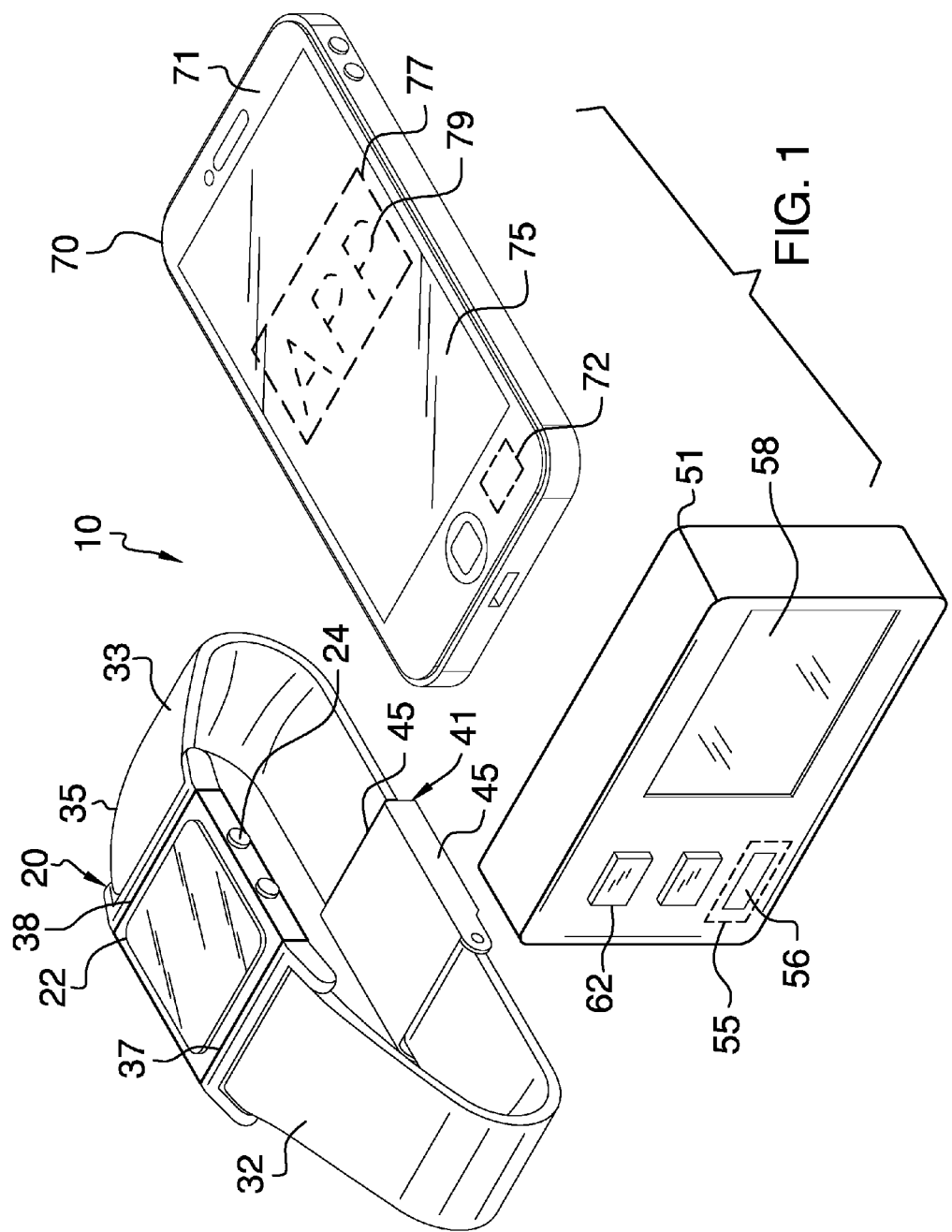
FIG. 1 is an isometric view of a cellular phone, a remote monitoring receiver unit with an LCD screen, and a wrist watch with a safety clasp lock.
Figure 2:
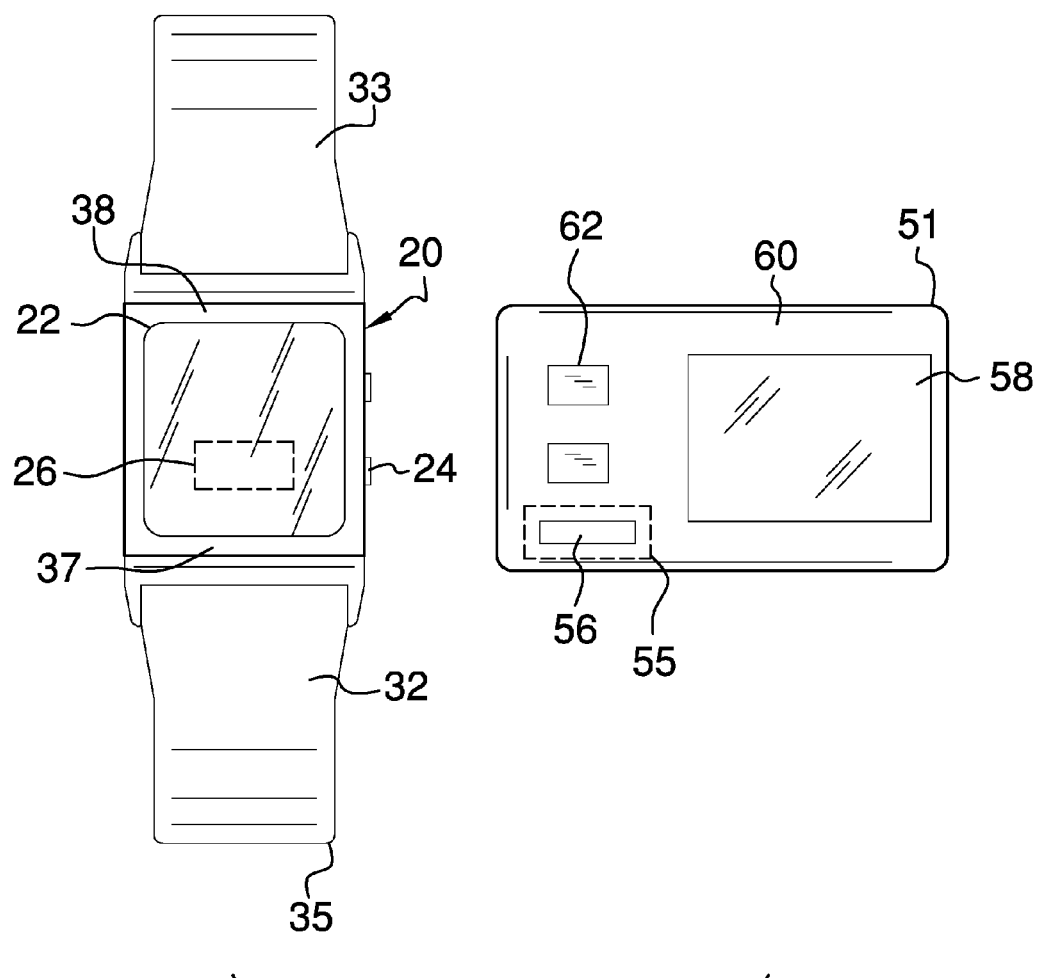
FIG. 2 is a top view of the wrist watch and the receiver unit.
Figure 4:
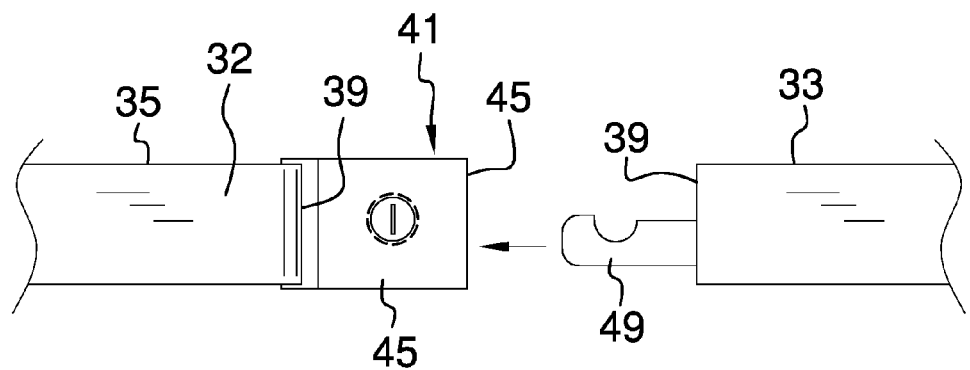
FIG. 4 is a side elevation view of the wrist watch.
Figure 3:
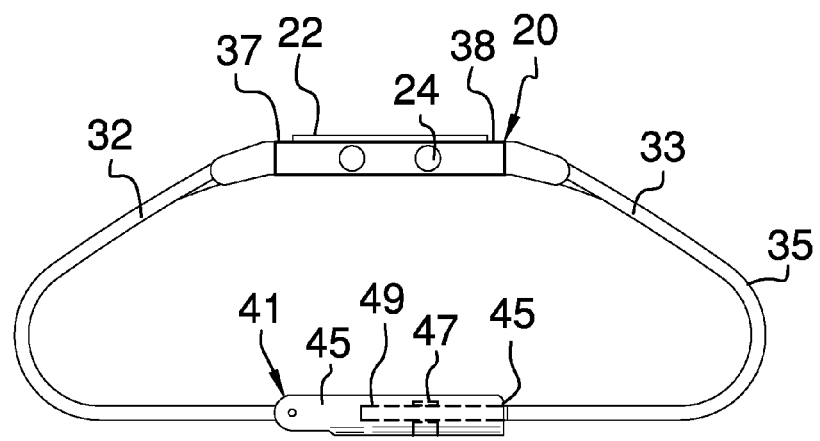
FIG. 3 is a detail view of the safety clasp lock of the wrist watch.
Figure 5:
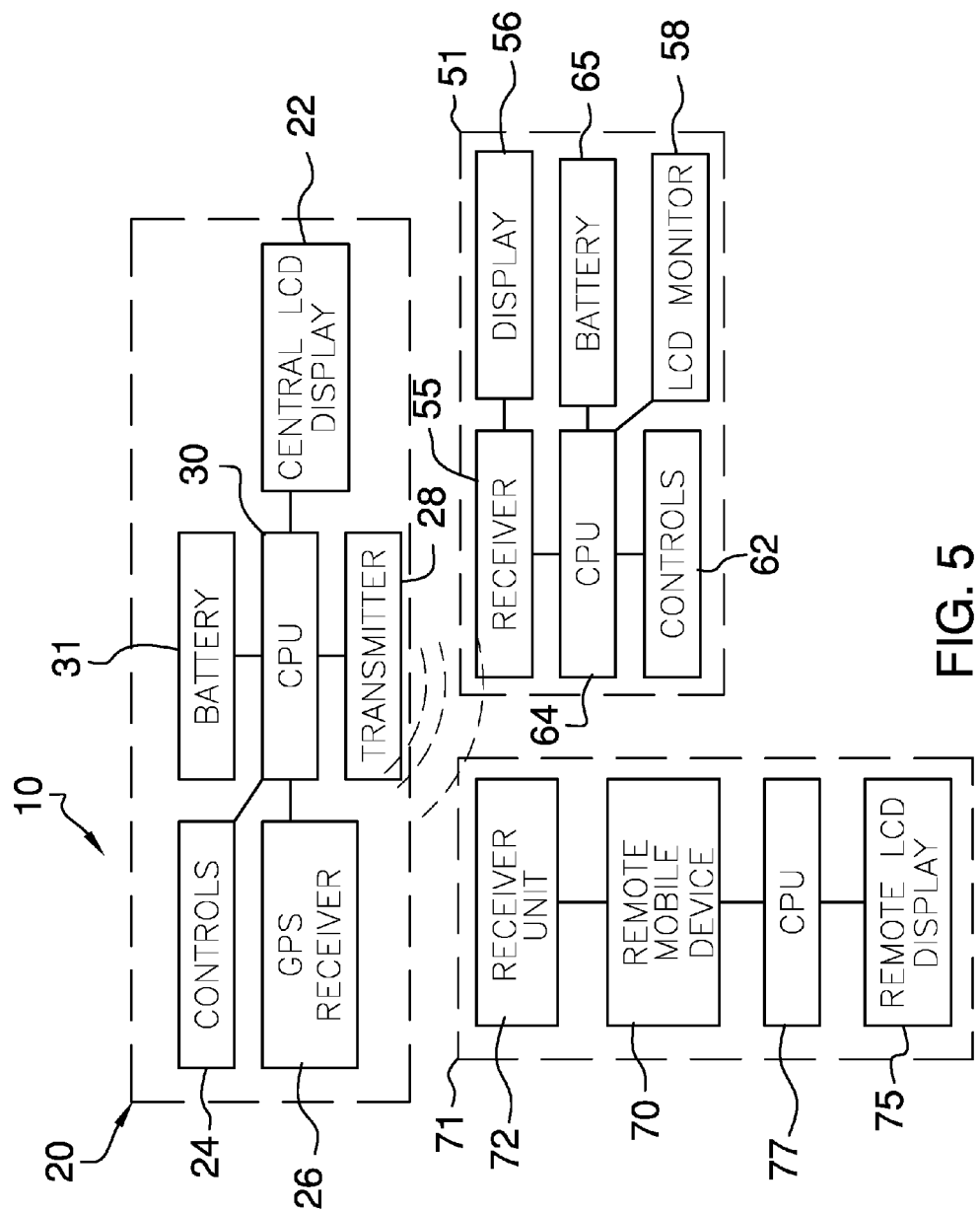
FIG. 5 is a block diagram of operations.

With reference now to the drawings, and in particular FIGS. 1 through 5 thereof, an example of the instant child tracking device employing the principles and concepts of the present child tracking device and generally designated by the reference number 10 will be described.

Referring to FIGS. 1 through 5 the present child tracking device 10, devised to continuously monitor a distance of a child from a supervising adult, is illustrated. The child tracking device 10 includes a child-worn wrist watch 20. The wrist watch 20 includes a central liquid crystal display 22 and at least one control button 24 disposed proximal the central liquid crystal display 22. A global positioning system receiver 26 and a transmitter 28 are disposed within the wrist watch 20. A battery-operated first central processing unit 30 is disposed within the wrist watch 20 and is in operational communication with the central liquid crystal display 22, the at least one control button 25, the global positioning receiver 26, and the transmitter 28. A battery 31 is disposed within the wrist watch 20 to serve as a power source. A first portion 32 and a second portion 33 of a wrist band 35 are attached to the central liquid crystal display 22 on a bottom end 37 and a top end 38, respectively, of the central liquid crystal display 22. Each of the first and second portions 32, 33 of the wrist band 35 has a distal end 39.

A safety clasp lock 41 directly interconnects the first and second portions 32, 33 of the wrist band 35 together to prevent the wrist watch 20 from being easily removed by the child wearing the wrist watch 20 or by a kidnapper. The safety clasp lock 41 has a parallelepiped clasp housing 43 pivotably disposed on the distal end 39 of the first portion 32 of the wrist band 35. The clasp housing 43 has an open external end 45 and a cylindrical rotational lock mechanism 47 laterally disposed within the clasp housing 43. The lock mechanism 47 has an open position and an alternate closed position corresponding to the release of and interconnection of the second portion 33 from and to the first portion 32. A hook 49 is disposed on the distal end 39 of the second portion 33 of the wrist band 35 and engages the lock mechanism 47 through the open external end 45. Upon the rotation of the lock mechanism 47 toward and alternately away from the distal end 39, the lock mechanism 47 locks and alternately releases the hook 49 therefrom.

A remote monitoring receiver unit 51 for use by the supervising adult to monitor the child's location is also provided. The remote monitoring receiver unit 51 includes a receiver 55 disposed therein which is in wireless communication with the transmitter 28 of the wrist watch 20. An LCD receiver display 56 and a LCD monitor 58 are disposed on a front side 60 of the remote receiver unit 51. At least one control switch 62 is disposed on the remote receiver unit 51 proximal the LCD monitor 58. A second central processing unit 64 powered by a battery 65 is disposed within the remote receiver unit 51 and is in operational communication with the receiver 55, the LCD receiver display 56, the LCD monitor 58, and the at least one control switch 62.

A remote mobile device 70, such as a cellular phone 71, is also provided for use by the supervising adult to monitor the child's location. The remote mobile device 70 includes a receiver unit 72 in wireless operational communication with the transmitter 28 disposed within the wrist watch 20, a remote LCD display 75, and a third central processing unit 77. The third central processing unit 77 has at least one software application 79 installed thereon and is in operational communication with the receiver unit 57 and the remote LCD display 75. The central processing unit 30 of the wrist watch 20 calculates the distance a signal from the transmitter 28 traveled to be received by each of the receiver 55 disposed within the remote monitoring unit 51 and the receiver unit 72 disposed within the remote mobile device 70. Upon calculation of a distance traveled by the signal greater than a predetermined safe distance from each of the receiver 55 and the receiver unit 72, an alert notification is displayed on each of the LCD receiver display 56, the LCD monitor 58, and the remote LCD display 75. The at least one software application 79 includes a global positioning system navigation map displayed on the remote mobile device 70, wherein the global positioning navigation map is configured to display the global position of a wearer of the wrist watch 20, and wherein the software application 79 is configured to maintain a continuous record of the global position of the wearer of the wrist watch 20. In addition, the at least one software application 79 is configured to permit designation of a geographical zone on the global positioning system navigation map. Upon the designation of a geographical zone, if the wearer of the wrist watch 20 is located outside of the geographical zone, an alert message is displayed on each of the LCD receiver display 56, the LCD monitor 58, and the remote LCD display 75. The at least one control button 24 on the wrist watch 20 and the at least one control switch 65 of the remote receiver unit 51 permit the supervising adult to control and set the parameters for operations, such as setting the predetermined safe distance from each of the receiver 55 and the receiver unit 72 from the wrist watch 20.

What is claimed is:

1. A child tracking device configured to continuously monitor a distance of a child from a supervising adult and a location of the child, the child tracking device comprising:
   a child-worn wrist watch comprising:
      a central liquid crystal display;
      at least one control button disposed proximal the central liquid crystal display;
      a global positioning system receiver disposed within the wrist watch;
   a transmitter disposed within the wrist watch;
      a battery-operated first central processing unit disposed within the wrist watch, the central processing unit being in operational communication with the central liquid crystal display, the at least one control button, the global positioning receiver, and the transmitter;
      a first portion and a second portion of a wrist band attached to the central liquid crystal display, the first portion and the second portion disposed on a bottom end and a top end, respectively, of the central liquid crystal display, each of the first and second portions of the wrist band having a distal end;
      a safety clasp lock directly interconnecting the first and second portions of the wrist band together;
   a remote monitoring receiver unit comprising:
      a receiver disposed within the remote monitoring receiver unit, the receiver in wireless communication with the transmitter of the wrist watch;
      an LCD receiver display disposed on the front side of the remote monitoring receiver unit;
      an LCD monitor disposed on a front side of the remote monitoring receiver unit;
      at least one control switch disposed on the remote receiver housing proximal the LCD monitor;
      a battery-operated second central processing unit disposed within the remote monitoring receiver unit, the second central processing unit in operational communication with the receiver, the LCD receiver display, the LCD monitor, and the at least one control switch;
   a remote mobile device comprising:
      a receiver unit in wireless operational communication with the transmitter disposed within the wrist watch;
      a remote LCD display;
      a third central processing unit having at least one software application installed thereon, the third central processing unit being in operational communication with the receiver unit and the remote LCD display;
      wherein the central processing unit of the wrist watch calculates the distance a signal from the transmitter traveled to be received by each of the receiver disposed within the remote monitoring unit and the receiver unit disposed within the remote mobile device;
      wherein upon calculation of a distance traveled by the signal greater than a predetermined safe distance from each of the remote monitoring unit and the receiver unit, an alert notification is displayed on each of the LCD receiver display, the LCD monitor, and the remote LCD display;
      wherein the at least one software application includes a global positioning system navigation map displayed on the remote mobile device, wherein the global positioning navigation map is configured to display the global position of a wearer of the wrist watch, and wherein the software application is configured to maintain a continuous record of the global position of the wearer of the wrist watch.

2. The child tracking device of claim 1 wherein the remote mobile device is a cellular phone.

3. The child tracking device of claim 1 wherein the at least one software application is configured to permit designation of a geographical zone on the global positioning system navigation map, wherein upon the designation of a geographical zone, if the wearer of the wrist watch is located outside of the geographical zone, an alert message is displayed on each of the LCD receiver display, the LCD monitor, and the remote LCD display.

4. A child tracking device configured to continuously monitor a distance of a child from a supervising adult and a location of the child, the child tracking device comprising:
   a child-worn wrist watch comprising:
      a central liquid crystal display;
      at least one control button disposed proximal the central liquid crystal display;
      a global positioning system receiver disposed within the wrist watch;
      a transmitter disposed within the wrist watch;
      a battery-operated first central processing unit disposed within the wrist watch, the central processing unit being in operational communication with the central liquid crystal display, the at least one control button, the global positioning receiver, and the transmitter;
      a first portion and a second portion of a wrist band attached to the central liquid crystal display, the first portion and the second portion disposed on a bottom end and a top end, respectively, of the central liquid crystal display, each of the first and second portions of the wrist band having a distal end;
      a safety clasp lock directly interconnecting the first and second portions of the wrist band together, the safety clasp lock having a parallelepiped clasp housing pivotably disposed on the distal end of the first portion of the wrist band, the clasp housing having an open external end and a cylindrical rotational lock mechanism laterally disposed within the clasp housing, the lock mechanism having an open position and an alternate closed position, and a hook disposed on the distal end of the second portion of the wrist band, the hook engaging the lock mechanism, wherein upon the rotation of the lock mechanism toward and alternately away from the distal end, the lock mechanism locks and alternately releases the hook therefrom;
   a remote monitoring receiver unit comprising:
      a receiver disposed within the remote receiver housing, the receiver in wireless communication with the transmitter of the wrist watch;
      an LCD receiver display disposed on the front side of the remote receiver housing;
      an LCD monitor disposed on a front side of the remote receiver housing;
      at least one control switch disposed on the remote receiver housing proximal the LCD monitor;
      a battery-operated second central processing unit disposed within the remote receiver unit, the second central processing unit in operational communication with the receiver, the LCD receiver display, the LCD monitor, and the at least one control switch;
   a remote mobile device comprising:
      a receiver unit in wireless operational communication with the transmitter disposed within the wrist watch;
      a remote LCD display; and
      a third central processing unit having at least one software application installed thereon, the third central processing unit being in operational communication with the receiver unit and the remote LCD display;
   wherein the central processing unit of the wrist watch calculates the distance a signal from the transmitter traveled to be received by each of the receiver disposed within the remote monitoring unit and the receiver unit disposed within the remote mobile device;
   wherein upon calculation of a distance traveled by the signal greater than a predetermined safe distance from each of the remote monitoring unit and the receiver unit, an alert notification is displayed on each of the LCD receiver display, the LCD monitor, and the remote LCD display; and
   wherein the at least one software application includes a global positioning system navigation map displayed on the remote mobile device, wherein the global positioning navigation map is configured to display the global position of a wearer of the wrist watch, and wherein the software application is configured to maintain a continuous record of the global position of the wearer of the wrist watch.

5. The child tracking device of claim 4 wherein the remote mobile device is a cellular phone.

6. The child tracking device of claim 4 wherein the at least one software application is configured to permit designation of a geographical zone on the global positioning system navigation map, wherein upon the designation of a geographical zone, if the wearer of the wrist watch is located outside of the geographical zone, an alert message is displayed on each of the LCD receiver display, the LCD monitor, and the remote LCD display.

* * * * *